US008788279B2

(12) United States Patent  (10) Patent No.: US 8,788,279 B2
Hayes  (45) Date of Patent: Jul. 22, 2014

(54) INFORMATION MANAGEMENT AND COMMUNICATIONS SYSTEM FOR COMMUNICATION BETWEEN PATIENTS AND HEALTHCARE PROVIDERS

(75) Inventor: Daniel C. Hayes, Valparaiso, IN (US)

(73) Assignee: Yescorp, Inc., Valparaiso, IN (US)

( * ) Notice: Subject to any disclaimer, the term of this patent is extended or adjusted under 35 U.S.C. 154(b) by 736 days.

(21) Appl. No.: 11/975,261

(22) Filed: Oct. 18, 2007

(65) Prior Publication Data

US 2008/0140449 A1  Jun. 12, 2008

Related U.S. Application Data

(60) Provisional application No. 60/829,955, filed on Oct. 18, 2006.

(51) Int. Cl.
G06Q 50/00 (2012.01)
G06Q 40/00 (2012.01)

(52) U.S. Cl.
USPC .................................................. 705/2; 705/3

(58) Field of Classification Search
USPC ........ 705/2–3; 707/104.1; 600/300, 545, 483; 340/573.1, 539.11; 702/179; 717/106
See application file for complete search history.

(56) References Cited

U.S. PATENT DOCUMENTS

| | | | |
|---|---|---|---|
| 5,441,047 A * | 8/1995 | David et al. ................... | 600/483 |
| 5,722,418 A * | 3/1998 | Bro ............................. | 600/545 |
| 6,289,513 B1 * | 9/2001 | Bentwich ...................... | 717/106 |
| 7,034,691 B1 * | 4/2006 | Rapaport et al. ............ | 340/573.1 |
| 7,070,562 B2 * | 7/2006 | Bardy .......................... | 600/300 |
| 7,493,264 B1 * | 2/2009 | Kelly et al. ..................... | 705/2 |
| 2001/0012913 A1 * | 8/2001 | Iliff ............................. | 600/300 |
| 2002/0010596 A1 * | 1/2002 | Matory .......................... | 705/2 |
| 2002/0029157 A1 * | 3/2002 | Marchosky ..................... | 705/3 |
| 2002/0072933 A1 * | 6/2002 | Vonk et al. ..................... | 705/2 |
| 2002/0116227 A1 * | 8/2002 | Dick ............................ | 705/3 |
| 2003/0028399 A1 * | 2/2003 | Davis et al. .................... | 705/2 |
| 2003/0050803 A1 * | 3/2003 | Marchosky ..................... | 705/3 |
| 2004/0006488 A1 * | 1/2004 | Fitall et al. ..................... | 705/2 |
| 2004/0059599 A1 * | 3/2004 | McIvor .......................... | 705/2 |
| 2006/0036134 A1 * | 2/2006 | Tarassenko et al. .......... | 600/300 |
| 2006/0049936 A1 * | 3/2006 | Collins et al. ............ | 340/539.11 |
| 2006/0064323 A1 * | 3/2006 | Alleckson et al. ............... | 705/2 |
| 2006/0155513 A1 * | 7/2006 | Mizrahi et al. ................ | 702/179 |
| 2006/0155584 A1 * | 7/2006 | Aggarwal ........................ | 705/3 |
| 2006/0212484 A1 * | 9/2006 | Chaffin et al. ............. | 707/104.1 |
| 2007/0061393 A1 * | 3/2007 | Moore .......................... | 709/201 |

* cited by examiner

*Primary Examiner* — Lena Najarian
*Assistant Examiner* — Natalie A Pass
(74) *Attorney, Agent, or Firm* — Hartman Global IP Law; Gary M. Hartman; Domenica N. S. Hartman

(57) ABSTRACT

An information management and communications system for communication between patients and healthcare providers, including an automated interactive patient response system, and apparatus and software to create, configure, and manage the content and structure of the patient response system to provide secure standards-based outpatient health assessment monitoring, to include disease management, medication compliance, wellness program compliance, and general health screening.

16 Claims, 6 Drawing Sheets

HealthCall®
HEALTHCALL.COM

| Home | Monitor | Patient | Configure | Reports | | Find Patient | Search | Email Help | Logout |
|------|---------|---------|-----------|---------|---|---|---|---|---|
| View | Alert | | | | | | | Welcome HC Support | |

Monitor > View

Assessments to view: [Today ▼]  Show this level and higher:  At Risk: [At Goal ▼]  ☑ Missed  ☑ Evaluated  (Apply Filter)  ✚ Add

| NAME | DATE | RISK ↓ | SIGNS | SYMPT | CMPLC | LFSTYL | PROG |
|------|------|--------|-------|-------|-------|--------|------|
| John Doe | 2006-03-06 | High | POS-1 | NEG | NEG | NEG | CHF |
| Sally Doe | 2006-03-06 | High | POS-1 | NEG | NEG | NEG | CHF |
| John Doe | 2006-03-06 | High | NEG | POS-1 | NEG | NEG | CHF |
| Sally Doe | 2006-03-06 | High | POS-1 | NEG | NEG | NEG | CHF |
| John Doe | 2006-03-06 | High | POS-1 | NEG | NEG | NEG | CHF |
| Sally Doe | 2006-03-06 | Med-High | NEG | POS-2 | NEG | NEG | CHF |
| John Doe | 2006-03-06 | Low | NEG | POS-2 | NEG | NEG | CHF |
| Sally Doe | 2006-03-06 | Low | NEG | POS-1 | NEG | NEG | CHF |
| John Doe | 2006-03-06 | Low | NEG | NEG | POS-1 | NEG | CHF |
| Sally Doe | 2006-03-06 | Low | NEG | POS-1 | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |
| Sally Doe | 2006-03-06 | At-Goal | NEG | NEG | NEG | NEG | CHF |
| John Doe | 2006-03-06 | At-Goal | NEG | NEG | NEG | NEG | CHF |

Figure 2

HealthCall®
HEALTHCALL.COM

Email Help | Logout

| Home | Monitor | Patient | Configure | Reports | Find Patient [Search] |
|------|---------|---------|-----------|---------|----------------------|

Welcome HC Support

| Status | Meds | Visits | Info | History |
|--------|------|--------|------|---------|

History  Extra Dose                                    ➕ Add

Patient > Meds                                      John Doe

| Name | Dose | Units | Route | Freq | Start Date | Comment |
|------|------|-------|-------|------|------------|---------|
| Toprol XL | 50 | mg | PO | qAM | Thu, Sep 22 | |
| Toprol XL | 25 | mg | PO | qPM | Thu, Sep 22 | |
| Coumadin | 2 | mg | PO | daily | Thu, Sep 22 | |
| Nitropatch | 0.2 | mg | PATCH | daily | Thu, Sep 22 | |
| Foltx | 1 | tab | PO | daily | Thu, Sep 22 | |
| Lanoxin | 0.25 | mg | PO | daily | Thu, Sep 22 | |
| Protonix | 40 | mg | PO | daily | Thu, Sep 22 | |
| Lasix | 40 | mg | PO | daily | Thu, Sep 22 | |
| Vasotec | 10 | mg | PO | bid | Thu, Sep 22 | |

Figure 3a

INFORMATION MANAGEMENT AND COMMUNICATIONS SYSTEM FOR COMMUNICATION BETWEEN PATIENTS AND HEALTHCARE PROVIDERS

This application claims the benefit of U.S. Provisional Patent Application Ser. No. 60/829,955, filed Oct. 18, 2006.

BACKGROUND OF THE INVENTION

While the United States healthcare system is being asked to do more with less, it is also being required to improve quality. Initiatives are underway that will provide financial incentives for hospitals and physicians to encourage improved outcomes and will penalize providers that achieve poor outcomes. In the Mar. 16, 2006, edition of the New England Journal of Medicine, a study conducted by the Institute on Healthcare Improvement at Harvard University determined that only 55% of Americans are receiving appropriate care.

Today, many of the nation's approximately 7,000 community hospitals and health care facilities face similar challenges to improve patient care and to improve patient outcomes while facing a constrained healthcare budget and while further stressing a limited healthcare staff.

This reality affects a broad area of medicine, including the treatment of patients with heart failure, diabetes, bariatrics, prenatal, and the care of patients before and after outpatient procedures and surgery. For example, heart failure is the most common admitting diagnosis in US hospitals, and the numbers of people with chronic diseases are increasing. Readmission rates for heart failure are 20% at 30 days, and 50% at 6 months. Mortality rates are 12% at 30 days, 33% at 12 months and 50% at 4 years. Because of these disturbing trends, Medicare, the Joint Commission and others have identified heart failure outcomes as core measures of quality.

An abundance of evidence suggests that the best way to increase the level of quality care for the growing patient population is to work more closely with the patient to monitor and track their individual progress, and to exercise preventative intervention when necessary. Recently, the American College of Cardiology/American Heart Association Practice Guidelines for heart failure management recommend the use of disease management systems for heart failure.

SUMMARY OF THE INVENTION

The present invention provides a solution in an advanced system of information management and communications technologies designed to provide better, more informed communication between patients and their healthcare providers through out a broad range of medical uses and healthcare disciplines.

The information management and communications system of the present invention incorporates interactive voice response technology similar to systems currently used by pharmacies and insurance companies to allow patients to renew their prescriptions and to check on insurance coverage. Automated voice response systems are pervasive in society due to their ease-of-use, accessibility, and cost savings.

Though interactive voice response technology within disease management has been previously used, the information management and communications system of the present invention further provides the ability to facilitate the creation, configuring, and management of the content and structure of an automated call for use in numerous outpatient monitoring settings.

In the same way that a bank automated teller machine (ATM) enables banking clients to conduct a broad range of financial transactions without burdening staff, the information management and communications system of the present invention interacts directly with patients to collect current and relevant information that is conveyed in a standards-based methodology to their healthcare providers throughout a broad range of care including: health screening, wellness programs, general follow-up, and disease management.

The capability provided by the information management and communications system of the present invention may be expressed as providing an automated patient response solution, and because the present invention is the first system that can be used in the care of patients throughout various stages of life, the invention may also be expressed as providing management of the life cycle.

This system of the present invention innovation allows healthcare practitioners to easily create or reconfigure programs and assessment questions, all within a graphical user interface without programming knowledge and without waiting. The system of the present invention may be quickly deployed in the outpatient setting in conjunction with virtually any healthcare program, such as, for examples, Prenatal Care. A high-risk pregnancy population can be monitored for signs and symptoms relating to diet, exercise, vitamins, water, weight gain, blood sugar, and other psycho-social issues.

Weight Management. A clinical weight management population can be monitored for signs and symptoms relating to diet, exercise and weight loss progress for the patients and identify any challenges early and intervene to encourage participation.

Pre and Post Surgery. Pre-operative patients with co-morbid conditions that need to be in-check before surgery could be monitored, and post surgical care can be monitored in order to track complications and prevent repeat hospitalizations.

Diabetes Care. A diabetic population can be monitored to assure that behavior modification, diet, and medications are being properly addressed. Avoidable hospitalizations could be prevented by providing a program where patients who are failing are recognized early[9].

As a further example, a community hospital has developed a collaborative care heart failure treatment program, consisting of a cardiologist, an advanced practice nurse and a team of registered nurses. The program includes education for all patients admitted with a diagnosis of heart failure, an outpatient heart failure clinic, and telemonitoring using the information management and communications system of the present invention. Weight and self reported signs and symptoms were telephonically monitored. When weight and/or symptoms are outside of pre-set limits, the heart failure treatment plan is readjusted. Data on 91 high-risk heart failure patients, 53 males and 38 females was entered into a database. Average age was 75.6.

Readmission rates and length of stay were obtained from hospital records. Compared to their hospital admission history prior to starting in the program, overall readmission rates were reduced by 77%. Heart-failure-only readmissions were reduced by 72%. Comparing the 12 months prior to enrollment in the program, there was a 30% reduction in length of stay, resulting is a 64% reduction in patient days. In a subset analysis, diabetic patients had improved glycemic control and reduced readmissions.

As a yet further example, another study involving 282 heart failure patients demonstrated a 72% reduction in hospital readmissions by using the information management and communications system of the present invention. The study took place within two hospitals. In this combined study, 158 patients were monitored and 124 were in the control group.

These examples of the implementation of the information management and communications system of the present invention have demonstrated in published outcomes both clinical validity and the financial efficacy of the present invention.

For the first time the information management and communications system of the present invention provides a solution that embraces the broader age span of patient populations through out the lifecycle and addresses both rising healthcare costs and compromised medical treatment in that it lowers costs, builds patient loyalty, improves compliance, and increases quality of care.

Common to many solutions applied to the field of medicine, the first products on the market only address an urgent need for a specific patient population. Then after more research and proven outcomes, a more flexible and easier to use solution evolves. This scenario characterizes the technical innovations that distinguish the information management and communications system of the present invention over the prior art. The information management and communications system of the present invention provides a sophisticated technology that interacts directly with patients to collect current and relevant information that is conveyed in a HIPAA compliant, standards-based methodology to the patients' healthcare providers.

The information management and communications system of the present invention is positioned to address the paradigm shift that is occurring within healthcare, generally. There is an ongoing movement from reactive care, where treatment is provided after an acute episode, towards proactive care that emphasizes the prevention of exacerbations and complications. Examples of this paradigm shift are manifested in the rapidly growing adoption of preventative care programs.

The information management and communications system of the present invention provides the ability to facilitate the creation, configuring, and management of the content and structure of an automated call for use in numerous outpatient monitoring settings, including, disease management, wellness programs, medical compliance, and general follow-ups.

BRIEF DESCRIPTION OF THE DRAWINGS

FIG. 2 is screen shot of an exemplary main monitoring screen viewable by healthcare providers.

DETAILED DESCRIPTION OF THE PREFERRED EMBODIMENT

User Interface.—

To better understand how the preferred embodiment to date of the information management and communications system of the present invention (hereinafter the "System") works, the next two sections explain a typical usage flow for both a patient and a healthcare provider (practitioner). The following scenario highlights the use of the System in a disease management clinic with a congestive heart failure patient population.

Patient Access.—

Figure 1:
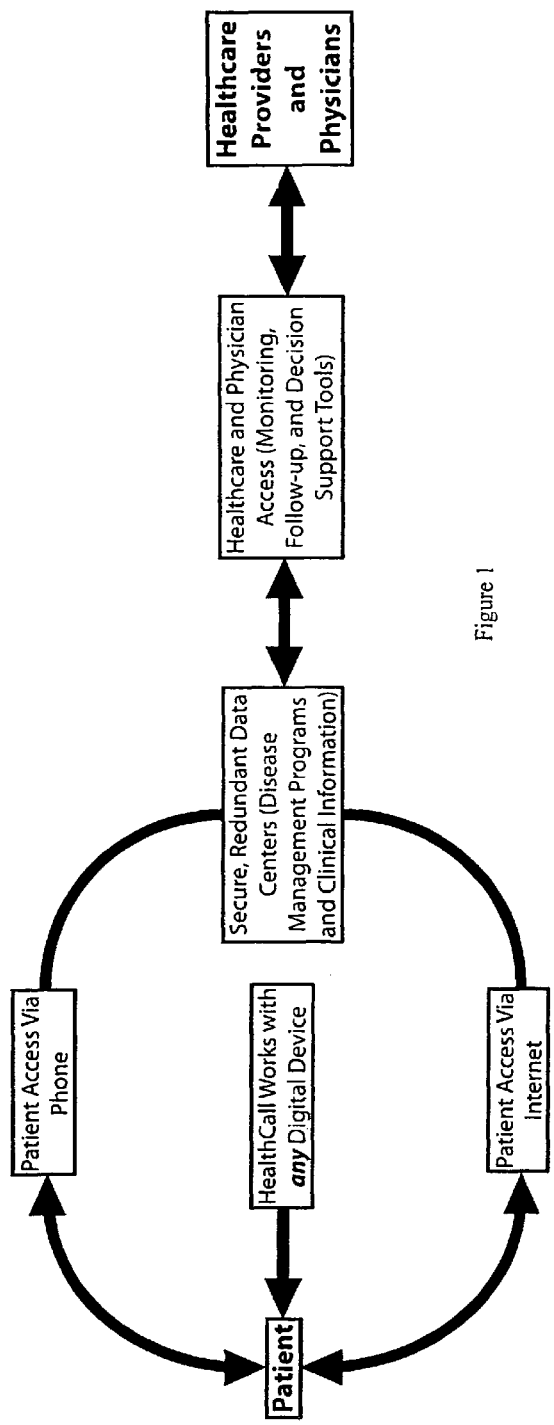
FIG. 1 is a schematic representation of the information management and communications system of the present invention, in which it is identified by the MYHEALTHCALL trademark.

Each patient receives a welcome packet with the toll-free number and instructions. Prior to calling in, he or she takes any needed health measurements (glucose level, body weight, temperature, etc.). The participant then simply calls in on the prescribed time interval or, the system can call the participant. The patient then answers the short health assessment questions that were chosen or defined by the physician. This information is immediately stored and analyzed by the System's decision support tools. Patients with elevated scores are identified for immediate intervention, and the appropriate healthcare individuals are notified. See FIG. 1.

Practitioner Access.—

Healthcare professionals, physicians and nurses access the System via a secured, encrypted connection to the Internet using a standard web browser such as Microsoft's INTERNET EXPLORER or Mozilla's FIREFOX. On the main monitoring screen, patients with elevated risk levels are prioritized and color-coded for immediate identification enabling management by exception. See FIG. 2. Instead of just monitoring 10 to 25 patients per day using prior art methods, with the System the healthcare provider can monitor 100 to 200 patients per day, depending upon the type of patient population.

Figure 3B:
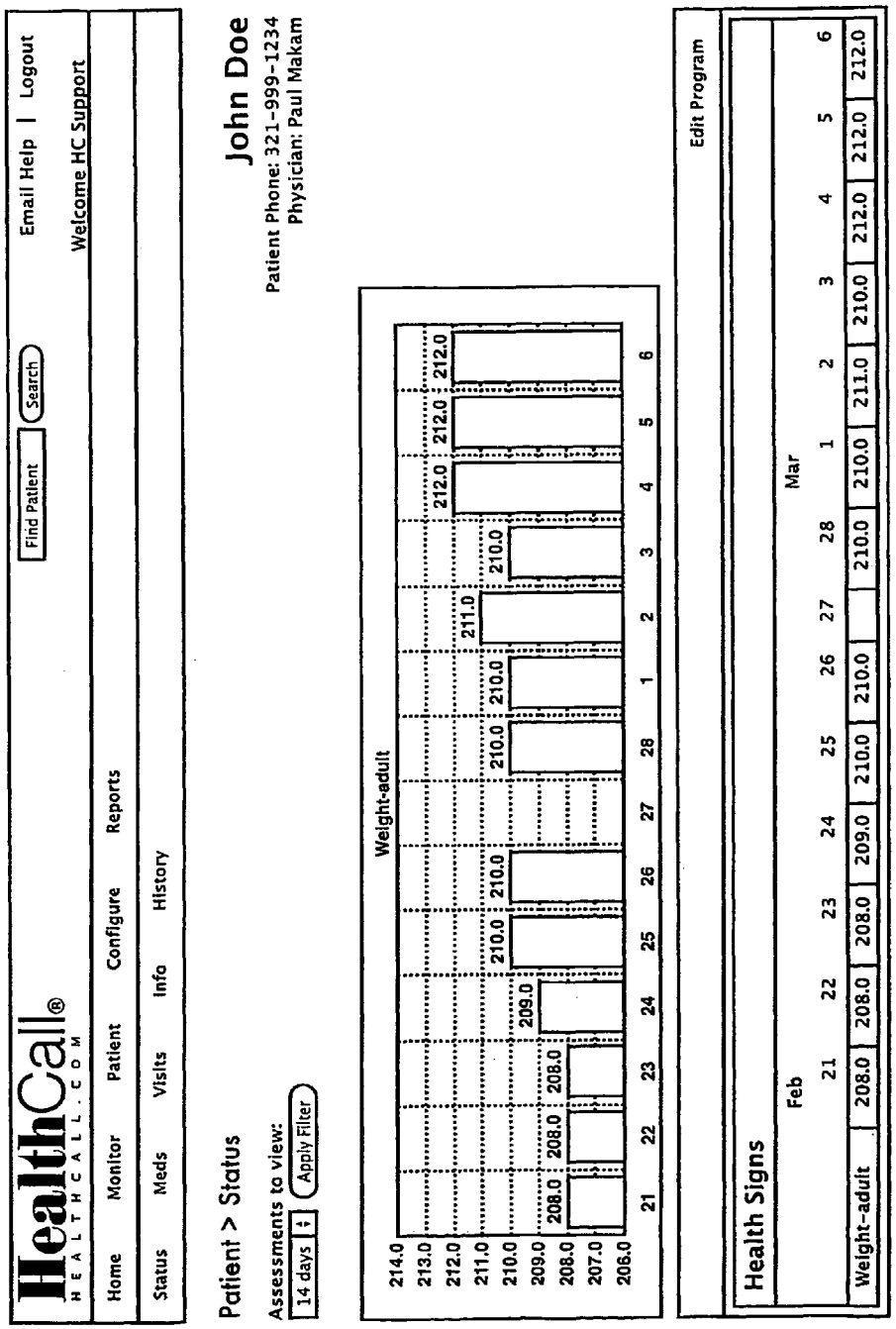
FIG. 3 is a screen shot of an exemplary complete status of the patient's self assessment that is visible after clicking on the patient's name in the main monitoring screen of FIG. 1.

Clicking on a patient's name within the main monitoring screen list reveals the complete status of the patient's self assessment, displaying self reported symptoms, self reported metrics, list of current medications, daily evaluation status, and a journal for comments. See FIG. 3.

Metrics such as a patient's weight, blood pressure, and blood sugar can be graphed to facilitate interpretation. Values outside of the prescribed limits are highlighted in red to further help identify risk indicators. Patient records can be fully annotated allowing an ongoing journal. All actions are automatically logged and archived. The System generates individual patient status reports for print or in electronic portable document format (PDF).

Software Architecture.—

The System is a provider-hosted application, meaning that the physician group, healthcare institution, or hospital does not need to purchase and maintain expensive servers and software. System administration is performed off-site, which eliminates or greatly reduces the effort required by the healthcare client's IT staff.

The System of the preferred embodiment to date currently runs on a proven platform comprised of a UNIX operating system, APACHE web server software, a middleware language similar to PHP, and a MySQL database. A number of other programming languages are employed, including html, xml, vxml, Java, and Java Script. This solution stack of technologies powers some of the largest and highest traffic web-based applications in use by Fortune 500 companies today.

Database independence. The MySQL database was chosen for initial development for reasons of speed, scalability, and low cost. The methodology employed to access the current MySQL database allows the transition to another, more robust database. One possible consideration is ORACLE. The use of MySQL-specific functions were avoided, and the higher order functionality was implemented within the application layer.

Figure 4:
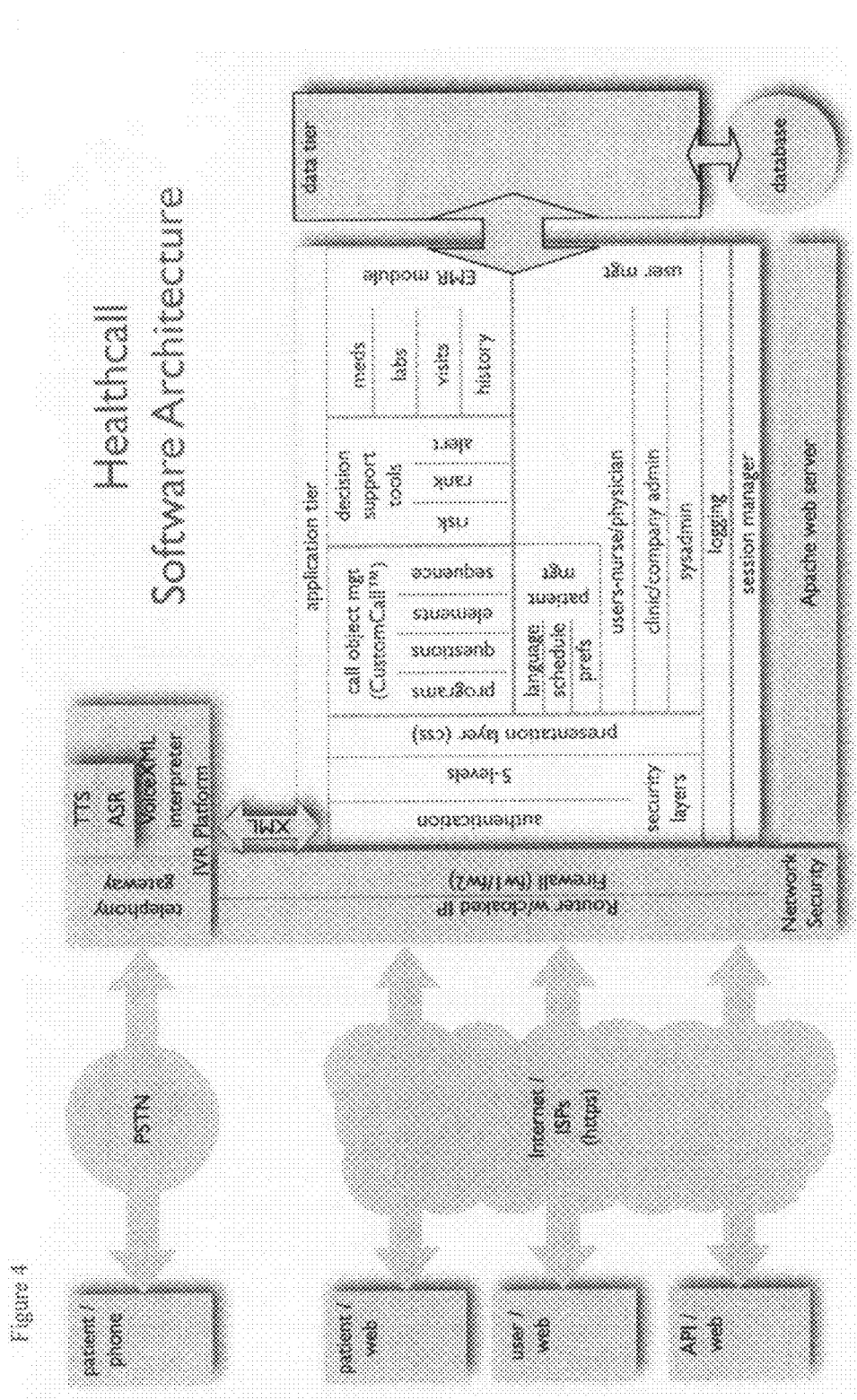
FIG. 4 is a diagram of the software architecture of the preferred embodiment to date of the information management and communications system of the present invention

The following sections provide an in-depth description of the software architecture diagram presented in FIG. 4.

Figure 5:
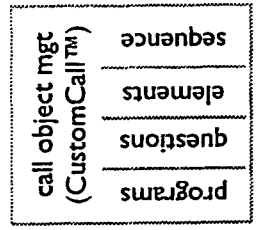
FIG. 5 is a diagram of the software architecture of the preferred embodiment to date for creating and editing patient programs and self assessment questions.

Call Management. The following functionality is related to how the healthcare professionals access, configure, and use Automated Patient Response Programs™ of the system These innovations allow healthcare practitioners to easily create and/or edit the programs and the patient self assessment questions. Additionally, they can configure the constructs of a completely new monitoring call and assessment questions, all within a graphical user interface without programming knowledge or having to wait. See FIG. 5.

User-Based Configuration. The architecture of the System allows the client to configure the structure (elements and sequence) of the monitoring call, including the greeting, login, instructions, self assessment questions, closing, disclaimer, etc. Preconfigured structures are built in, such as, for example, disease management, wellness programs, medical compliance, post surgery care, appointment reminder, and health screening. With this flexibility, the System can be quickly deployed in the outpatient setting in conjunction with virtually any medical program.

Here are four such scenarios.

Scenario 1: Heart Failure, Disease Management

A nurse practitioner is monitoring (tracking key signs and symptoms) of a population of high-risk heart failure patients in an outpatient setting.

In studies published by the Heart Failure Society of America, the risk of hospitalization for heart patients was over four times greater in patients who only received outpatient clinical care compared to patients who received outpatient clinical care plus personal monitoring, such as is now provided by the System.

In this Scenario 1, the nurse desires to add another patient to the heart failure program. The nurse first selects a standard list of Heart Failure Health self assessment questions. After reviewing the patient's unique needs, the nurse chooses an additional question that requests this patient's current glucose level, and then edits the standard Weight question to reflect both the patient's base weight and goal weight. Additionally, because this patient is obese, the nurse modifies one of the default Weight Alert rules from 3 pounds in 3 days, to 5 pounds in 3 days. The nurse chooses to have the System call daily at 9:00 AM, but excludes Wednesday because the patient travels on that day. Using a toll-free number, the patient will call in to update the patient's current status on Wednesdays.

The main steps of Scenario 1 have included:
Modifying the default Heart Failure Health program's self assessment questions.
Customizing the Heart Failure Health self assessment questions, rules, and schedule to individualize the care plan to meet the unique needs of the patient.
Scenario 2: High Risk Pregnancy, Wellness Program A registered nurse is monitoring a group of expectant mothers. Each mother is assigned to a System Pregnancy Program that is aligned with each trimester of fetal development. The System's Pregnancy Program assesses different signs and symptoms questions related to each trimester, and also varies in frequency of self assessments (number of times in a given period that a health assessment is collected).

In this Scenario 2, a woman is in her second trimester, and her physician wants to stay closely in touch due to her increased blood pressure level and possible risk of pre-eclampsia. In addition to the standard list of Pregnancy Program questions related to the wellness program, the physician selects to have this patient's blood pressure level and pulse rate monitored. Using a standard digital blood pressure cuff-based meter, the patient will enter her blood pressure and pulse rate along with answering a few symptom-related questions relating to getting enough sleep, avoiding caffeine, taking a daily supplement, and an additional question assessing swelling in her feet and ankles. The physician schedules to have her called 3 times a week on Monday, Wednesday, and Friday after 5:00 pm for the next 2 months. The patient also has the option to call in on any day should she notice an increase in her blood pressure on a non-scheduled day.

The main steps of Scenario 2 have included:
Editing the default Pregnancy Program Health self assessment questions.
Choosing the additional blood pressure and pulse rate health self assessment questions.
Scheduling the number of weekly calls and call duration.
Scenario 3: Post Open Heart Surgery, Medical Compliance In this Scenario, the nurse at a hospital desires to closely monitor a patient being released after having open-heart surgery two days prior. The physician selects the standard list of Post Surgery Health self assessment questions that had been created specifically for the type of procedures that they commonly perform (i.e., confirm that they understood their discharge instructions, and how to care of their incisions, prescriptions to take, etc.). He then edits the default list of 9 health self assessment questions and removes 2 questions not applicable to this individual patient. Due to special circumstances, the physician also chooses to have the patient's oxygen level monitored. Using a pocket-sized, standard digit finger pulse oximeter, the patient will enter his current SpO2 value along with answering the 7 symptom-related self assessment questions during his daily call. The nurse schedules to have the System call the patient daily after 8:00 AM for the next two weeks. Should the patient miss a System call, he can always initiate the health self assessment by calling the toll-free number at a more convenient time.

The main steps of this Scenario have included:
Editing the default Post Surgery list of health self assessment questions.
Creating and choosing an additional oxygen monitor survey question.
Scheduling the call frequency and duration.
Scenario 4: Patient Quality Survey, General Follow-Up In this Scenario, an administrator needs to collect quality data regarding patient satisfaction. This hospital discharges 600 patients per month. Using the System, they can create a quality survey program that calls each patient and asks them to rate the level of care they received relative to five competitive areas (e.g., promptness, cleanliness, friendliness, etc.), and also ask if the patient still has an unresolved problems or issues.

Programs and Assessment Questions.—Within the System's user interface, the healthcare professional can create or edit programs and self assessment questions. Programs are sets of self assessment questions based on standard treatment guidelines that encompass all of the key aspects of care for major diseases, disorders, and health practices. Questions are grouped by signs, symptoms, life style, and compliance, such as sign questions relate to metrics (weight, blood pressure, blood sugar, etc.), symptom questions (chest pain, shortness of breath, dizziness, edema, fatigue, etc.), life style questions (exercise, rehabilitation, diet, etc.) and compliance questions (taking prescribed medications, following procedures, post-surgery care, etc.)

In addition to providing current and relevant information directly to the healthcare professional, System programs also serve to help educate and reinforce positive behavioral lifestyle choices in patients using the System.

Healthcare professionals can use any of the System's standard programs, which include congestive heart failure (CHF), asthma, chronic obstructive pulmonary disease (COPD), coronary artery disease (CAD), diabetes, lipid, nutrition, osteoarthritis, pre/post surgery, pregnancy, stress management, weight management.

When using the System, standard programs can be edited, or new programs can be created for specific patient populations, or for individual patients.

Figure 6:
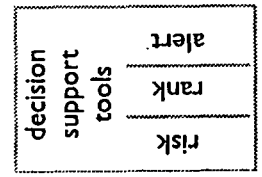
FIG. 6 is a diagram of the software architecture of the preferred embodiment to date for alerting and individual or group via pager, e-mail, or text message.

Decision Support Tools. Decision support tools analyze the risk level of the health self assessment in real time. As each self assessment is completed by a patient, the System's decision support tools evaluate each of the patient's positive answers, individually and collectively, against a predictive model associated with the particular program and the disease/condition. Patients with elevated risk levels are ranked within the patient population. This ranking is displayed within the main monitor screen in color-coded degrees of risk, high, med-high, med-low, low, and at-goal. Future System enhancements will include the ability to alert an individual or group via pager, email, or text message. See FIG. 6.

Depending upon the disease or medical condition, each sign and symptom question, and groups of questions will represent different levels of risk or predictors of an impending medical event. The decision support tools enable the risk levels for each question to be individually set within each program.

Predictive modeling is an important part of the System's decision support tool set. For example, the System's predictive modeling methodology identifies patients with a high statistical probability of risk for pending cardiac events. There are a few methodologies for assessing risk of impending heart disease. The FRAMINGHAM index is one well-known methodology. A preferred predictive modeling methodology used in the System to date uses a broader range of patient history, lifestyle habits, and current health signs to more accurately predict impending heart failure.

Figure 7:
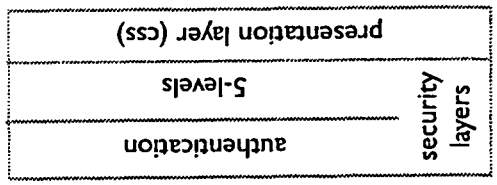
FIG. 7 is a diagram of the software architecture of the preferred embodiment to date for the security layers, logging and presentation layer.

Framework. The framework manages the security layers, logging, and presentation layer. The security implementation manages the user permissions, user access, validation, and content permissions. Content permission is based upon 5 levels of control: the business entity, the hierarchy of the type of user (systems, company, and clinic administrator), the role of the user (patient, nurse, physician, administrator), and the relationship to any given content in related time. The framework tracks all transaction, record, and user logging of key actions (who, what, where, when). The presentation layer, or screen builder, relates to the cosmetics of how the application looks and how different content is presented to users on different platforms. Cascading style sheets (CSS) are used extensively to enable different "presentations" of the content for standard browsers, printing, table PCs, and PDA devices such as Palm Treo, and HP iPAQ Pocket PCs. See FIG. 7.

PHI Access and Security. This section focuses specifically on the methodology the System employs to securely access protected health information (PHI) and comply with related HIPAA regulations (Health Insurance Portability and Accountability Act).

Although HIPAA was passed into law in 1996, most covered entities had until April 2005 to comply with the final Security Rule. Today, many medical information technology applications still use similar security access models used in the business world. Most information technology solutions for business grant access based upon the hierarchy and/or role of the user. While there is a hierarchy within healthcare organizations and the professionals that work there do have specific roles, neither of these criteria directly relate to who should have the access to specific personal medical information.

The preferred System to date uses a time-aware, protected access model that is based upon a direct and indirect relationship to each patient. This is unique in that other systems typically grant record access based upon the type of user, group, role, or a hierarchy of user permissions in which the higher level of access provides greater access to patient information. These current access models are less than optimal and may not conform to HIPAA guidelines.

Conversely, in accordance with HIPAA guidelines, the System allows patient record access based upon the actual relationship of the healthcare professional to the patient. For example, a patient grants access of his or her medical information to those physicians who are providing direct care. Within the System, a direct (logical) relationship is created between the patient and physician. A physician's nurse needs to access the patient's records to report laboratory data. Within the System, a direct (logical) relationship is created between the physician and this physician's nurse, thereby creating an indirect relationship to the patient and gaining access. While these examples are greatly simplified, the System time-sensitive, protected access model does represent a more robust approach to maintaining access to protected health information over time.

In general, the System is definable as providing a method for creating, editing, and assessing a customized call flow, and a method for securely accessing protected health information. For each method, a "storage mechanism" refers to a device that records and retrieves data required by the methods. The best solution to date for the System has been to use a RDBMS (relational database management system) that supports transactions, roll-back, and referential integrity, such as the RDBMS provided by ORACLE.

The preferred embodiments to date of these System methods are described in the following Examples.

EXAMPLE 1

Method for Creating, Editing, and Assessing a Customized Call Flow

The method for creating and editing a customized call flow includes the use of a graphical user interface and a storage mechanism. A "call flow" means the entire automated interaction, including the dialog and response between the system and the person on the phone.

Graphical Interface. The graphical user interface allows a user to interactively build a call flow using "Call Objects" (described below); each Call Object is positioned and configured by the user to comprise the entire dialog of the call. Once completed, the call flow is recorded using the storage mechanism as a "template" and is used to provide an individualized, automated interactive experience.

Call Objects. As defined herein, a Call Objects represents an individual element within the call. Call Objects include, but are not limited to, Authentication, Greeting, Announcement, Closing, Conditional Announcement, Third-Party Announcement, Interactive Prompt, Notice, Disclaimer, and Conditional. Each is described below:

Authentication—This allows the user to authenticate the person on the call. It is further described below.

Greeting, Announcement, Closing—This allows the user to include an announcement in the call flow. This announcement is always played during the call flow.

Conditional Announcement—This allows the user to include a conditional announcement in the call flow. This announcement may be played during the call flow, depending on if the user-specified condition is satisfied. The conditionals supported are covered below.

Third-Party Announcement—This allows the user to include a conditional "third-party" announcement in the call flow. This announcement may be played during the call flow, depending on if the user-specified conditional is satisfied. The conditionals supported are covered below. A "third-party" is anyone other than the callee or caller.

Interactive Prompt—This allows the user to include a prompt in the call flow. This prompt will require a response, which may then be used for a conditional and/or be used for collecting data (which is then recorded in the storage mechanism). More specifics about Interactive Prompt is provided below.

Notice—This allows the user to include a notice in the call flow. This notice is often of a legal or medical nature and is always played during the call flow.

Disclaimer—This allows the user to include a disclaimer in the call flow. This disclaimer is a legal notice and is always played during the call flow.

Conditional—This allows the user to include a conditional in the call flow. This conditional object allows branching in the call flow and may be used to repeat segments of the call, or customized paths depending on the conditional. The conditionals supported are covered below.

Authentication.—A customized call flow can be initiated by either the system calling the intended person, or the intended person calling the system. "Intended person" is the person the customized call flow is setup for; some examples include a patient, a participant in a study, and a participant in a wellness program.

In the case of the System calling the intended person, the customize call flow will prompt the unauthenticated person who answers the phone to confirm they are the intended person by requesting they press one on their telephone keypad. The customized call flow will then authenticate them as the intended person by requesting the intended person enter their personal identification number (PIN) and comparing their response to the PIN stored in the intended person's account to ensure they match.

In the case of the intended person calling the System, the customized call flow will perform a caller identification to try to determine the possible identity of the caller. Should that fail, the customize call flow will then request the caller enter their account-associated phone number. Once the possible identity of the caller is established, the customized call flow will then authenticate them by requesting the intended person enter their personal identification number (PIN) and comparing their response to the PIN stored in the intended person's account to ensure they match.

Pre-Recorded Media, Custom-Recorded Media, and Text-To-Speech Media.—For each Call Object, the user may (1) select pre-recorded media, (2) choose to create custom media, or (3) choose to have the transcript converted to speech via Text-To-Speech (TTS). The TTS option is automatically used when no other media is available, regardless of the selection originally made by the user.

Each Call Object supports multiple languages by allowing multiple media per language.

For custom media, the user may either upload media, or the user may choose to record the media via the phone or other input device. In the latter case, the user may call or log in to record the message, or may choose to be called to record the message. In all cases, the user may choose to have a third-party record the media on their behalf.

For Text-To-Speech, the user may choose the "voice" in which it is read. This may be selected as a global preference for the call, or may be individually selected on a per-call-object basis.

Randomized Call Objects.—For each Call Object, there is an option to provide more than one media choice per language and have one media randomly selected to use during the Customized Call Flow. The selection is either truly random, with all media having equal weight, or a weighted-random, where either (1) voice files are assigned "weights" with the most weighted voice files selected more often or (2) voice files not selected as often will have a greater chance of being selected.

Conditionals.—

For every conditional object, the user may select one or more conditions by which to return a binary or enumerated response. The conditions may be combined using logical AND, logical OR, logical XOR and grouped to allow any logical expression. The conditionals include, but are not limited to: Date, Time, Attribute, Prompt, and Random. Each is described below:

Date—Allows a conditional based on the date, including a specific date, a range of dates, the month, the day, the year, the day of week, or the week of year.

Time—Allows a conditional based on the time, including a specific time, a range of times, the hour, the minute, or the second.

Attribute—Allows a conditional based on a known attribute of the person on the call. Some examples: age, gender, medical condition, language preference, inbound phone number, outbound phone number, location, caller ID, etc.

Prompt—Allows a conditional based on a response given to an "Interactive Prompt" Call Object earlier in the call flow.

Random—Allows a conditional based on a random selection.

Interactive Prompt.—The Interactive Prompt allows for a variety of responses, including, but not limited to, the following:

Numerical response—one or more digits interpreted as a single number (e.g. 3415=Three-thousand, four-hundred, fifteen).

Sequenced response—one or more telephone key presses (e.g. *2=star 2).

Scaled response—entering one or more digits that correspond to a scale (e.g. on a scale of 1 to 5, 1 is least favorable, 5 is most favorable).

Interpreted response—entering two or more digits that are interpreted in a format differing from the actual number entered. For example, rather than entering two values for blood pressure (systolic and diastolic), an interpreted response allows entering 12080 which is interpreted as 120/80. Another example is decimal weight; entering 1834 would be interpreted as 183.4. Another example is height; entering 511 would be interpreted as 5 feet, 11 inches. Another example is time; entering 1321 would be interpreted as 1:21 pm.

For all types of Interactive Prompts, the user may choose to require a value to be submitted, or allow the Interactive Prompt to be skipped.

For all types of Interactive Prompts, the user may choose to allow multiple values to be entered; the number of multiple values allowed may either be fixed finite (e.g. require 3 values), range finite (e.g. 1 to 3 values) or unlimited.

For each Interactive Prompt, the user may assign the relative risk of a given answer, in relation to the entire data collected from the Customized Call Flow. The user may choose to use the default risk value (if any), or may choose to customize the risk value given the patient population history or circumstances. The risk value is then aggregated into an overall risk for the patient (see Method 2).

The relative risk may be implemented in any way that allows a comparison operation between two risks, with the outcome denoting which of the two risks is higher.

Individualized Call Flow.—It is possible to further customize any call flow template, providing an individualized call flow on a patient-by-patient basis.

Assessing the Results of a Customized Call Flow.—Assessing the results of a customized call flow requires aggregating the relative risk factors for each answer provided and may include factoring in historical data or other evidence.

Each answer is evaluated for its relative risk factor using one or more risk evaluations. Some examples of risk evaluations are comparing the current answer to a baseline value, comparing the current value to a maximum value allowed, a minimum value allowed, the relative change over a number of days, or other comparative measures. The relative risk factor will evaluate to one of the following risks assessments: High, Medium-High, Medium-Low, Low, At-Goal/Within Limits ("Within Limits" is the more common medical term). They are related by their weights as 1 "High," 2 "Medium-High," 3 "Medium-Low," 4 "Low." Therefore, a single answer with the relative risk factor of "High" has as much risk as two answers that have the relative risk factor of "Medium-High," and so on.

To aggregate the relative risk factors, their relative weights are combined and evaluated, with the final weight being the result of the aggregate. For example, if the customized call flow recorded five answers, of which three were assessed as "At Goal," one was assessed as "Medium-High" and one was assessed as "Medium-Low," the aggregate relative risk would be "Medium-High."

In addition, historical or other evidence may be used to adjust the risk for individuals. For example, this allows for the case where the customized call flow collects information on ankle swelling, yet the patient lost their legs in an automobile accident.

Managing Patient Populations by Exception.—Managing an at-risk patient population makes use of a graphical user interface that displays a list of patients broken out by group (see Example 3). Included in the list of patients is the name of the patient, their relative risk (see "Assessing the Results of a Customized Call Flow" above), and the number of questions that evaluated as a risk. The list of patients is color coded, such that each patient is assigned a color based on their relative risk. Each relative risk has a corresponding color to allow easy identification of patients with the highest risk. In addition, the list is sortable, which allows the highest risk patients be sorted to the top, and remainder sorted by their relative risk. It also is filterable, which allows hiding patients in the list that don't meet the criteria (typically Low risk or At-Goal patients).

EXAMPLE 2

Method for Securely Accessing Protected Health Information

The method for securely accessing protected health information makes use of a storage mechanism, a security model, user information, patient information (protected health information), relationship information and enforcement.

Security Model.—The security model is a set of rules applied systematically to the user, based on their user information, to determine the level and scope of permission allowed for accessing protected health information (patient information). The term "care provider" is used generically to describe a physician, a nurse, a health practitioner, a health coach, or any other individual charged with providing direct or indirect care. The rules for care providers are as follows:
1. Does the user have a direct one-to-one care provider relationship with the patient (e.g. a physician of the patient)?
    a. If yes, allow the user to view the patient information.
2. If no, does the user have a supporting care provider relationship with another user that has a direct one-to-one care provider relationship with the patient (e.g. a nurse of a physician of the patient)?
    a. If yes, allow the user to view the patient information.
3. If no, does the user have a supporting care provider relationship with the patient via a Virtual Clinic (see Method 4)?
    a. If yes, allow the user to view the patient information.
4. If no, disallow the user to view the patient information.

In all cases, the user must agree to one or more compliance statements for the protected health information the first time they access it for the patient (e.g. HIPAA). In all cases the relationships are finite in duration: the relationship duration and renewal is determined by the patient.

User Information.—User information is held in the Storage Mechanism and is used to determine what, if any, permission is granted to view protected health information. A user may be of one or more roles, including, but not limited to, Physician, Nurse, Administrator, Clinic Administrator, Billing, Clerical, and/or Research. Each of these roles has predefined limits imposed on them to protected health information. The roles are defined as follows:
1. Physician—allowed full access to protected health information, as allowed by the Security Model.
2. Nurse—allowed full access to protected health information, as allowed by the Security Model.
3. Administrator—not allowed access any protected health information at any time.
4. Billing—limited access to only the patient's name, medical record locator identification and usage metrics required for billing.
5. Clerical—limited access to only the patient's contact information (name, phone, address) for adding/editing.
6. Research—limited access to aggregate data only.

Patient Information.—Patient information (protected health information) is held in the Storage Mechanism and access is granted to add, modify, or remove it based on the Method. Protected health information includes, but is not limited to, the patient's name, address, phone, medical record locator identification, medications, notes, history, lab work, and assessments collected.

Relationship Information.—Relationship information is held in the Storage Mechanism and contains the following types of relationships: Patient to Care Provider, Care Provider to Care Provider, Patient to Virtual Clinic, Care Provider to Virtual Clinic, Care Provider to Business, Business to Business.

Patient to Care Provider Relationship.—By creating a relationship between a Patient and a Care Provider, it allows the Care Provider to access the protected health information for the Patient (given the constraints of this Method).

Care Provider to Care Provider Relationship.—By creating a relationship between a Care Provider and another Care Provider, it allows the first Care Provider to access the protected health information for a Patient that has a relationship with the second Care Provider (given the constraints of this Method). For example, this allows a nurse to have a relationship with a physician and have access to his patients' protected health information. Patient to Virtual Clinic Relationship—By creating a relationship between a Patient and a Virtual Clinic, it allows the Patient to be grouped and managed with similar Patients (see "Managing Geographically-Disparate Patient Populations as a Single Group below").

Care Provider to Virtual Clinic Relationship.—By creating a relationship between a Care Provider and a Virtual Clinic, it allows the Care Provider to manage similar Patients (see "Managing Geographically-Disparate Patient Populations as a Single Group below").

Care Provider to Business Relationship—By creating a relationship between a Care Provider and a Business, it allows the Care Provider to be made available company-wide to potential patients, and to have extended relationships via the Business to Business Relationship (see below).

Business to Business Relationship—By creating a relationship between two business entities, it allows a Care Provider from one business to care for a patient cover by another business. For example, this allows a physician with a private practice to have a relationship with a patient at a hospital's Virtual Clinic.

Managing Geographically-Disparate Patient Populations as a Single Group.—Geographically-disparate patient populations are grouped based on similar disease state, condition or care plan that can be treated and managed as if the patient population were located in a single location. This requires creating two relationships: the Care Provider to Virtual Clinic and the Patient to Virtual Clinic. For any care provider that has a relationship with a Virtual Clinic and a patient has a relationship also with the Virtual Clinic, the care provider has access to that patient, within the constraints of this Method.

Enforcement.—Enforcement is the action of applying the security model rules to the user to determine the level and scope of permission allowed for accessing protected health information, then allowing or denying based on the permission determined.

I claim:

1. An information management and communications system for communications between a population of patients and healthcare providers and providing automated interactive health assessment monitoring of the population of patients that enables healthcare providers to selectively provide any of health screening, medical compliance, wellness program compliance, and disease management tailored for an individual patient within the population of patients, the system comprising:

a nontransitory storage mechanism of a computer network system and on which is stored a plurality of call objects, the call objects comprising a plurality of health assessment questions and at least one message chosen from the group consisting of authentication messages, greeting messages, announcements, closing messages, conditional announcements, third-party announcements, interactive prompts, notices, disclaimers, and conditional messages;

a graphical user interface of the computer network system and on which a healthcare provider interactively builds an entire monitoring call dialog that is audible and tailored for an individual patient by using the graphical user interface to select multiple call objects from the plurality of call objects including selecting the at least one message and selecting multiple health assessment questions from the plurality of health assessment questions, edit at least some of the multiple call objects including the multiple health assessment questions thereof and thereby further tailoring the monitoring call dialog for the individual patient, position and configure the multiple call objects and the multiple health assessment questions thereof and thereby creating and configuring a sequence of elements of the monitoring call dialog and thereby further tailoring the monitoring call dialog for the individual patient, and save the entire monitoring call dialog to the storage mechanism; and an automated interactive patient response system that audibly communicates the entire monitoring call dialog to the individual patient, enables the individual patient to provide responses to the multiple health assessment questions, and records the responses of the individual patient in the storage mechanism;

wherein the computer network system containing the storage mechanism and the graphical user interface provides secure health assessment monitoring of the individual patient, performs a risk evaluation based on the responses of the individual patient by aggregating relative risk factors obtained by comparing the responses of the individual patient to comparative measures, stores the risk evaluation on the storage mechanism, and enables a healthcare provider to access the responses of the individual patient and the risk evaluation stored on the storage mechanism, and modify the monitoring call dialog by editing at least one of the multiple health assessment questions and thereby further tailoring the monitoring call dialog to selectively provide any of health screening, medical compliance, wellness program compliance, and disease management of the individual patient.

2. The information management and communications system of claim 1, wherein the graphical user interface enables the healthcare provider to access the responses of the patient and the risk evaluation stored on the storage mechanism and is connected to the storage mechanism via the Internet.

3. The information management and communications system of claim 1, wherein the graphical user interface further enables accessing by a healthcare provider the storage mechanism and selecting by the healthcare provider additional health assessment questions from the plurality of health assessment questions after the healthcare provider has accessed the responses of the patient and the risk evaluation stored on the storage mechanism, and then communicate the selected additional health assessment questions to the patient.

4. The information management and communications system of claim 1, wherein the system is provider-hosted and the storage mechanism and portions of the computer network system that perform and store the risk evaluation are components of a server offsite from the graphical user interface.

5. The information management and communications system of claim 1, wherein for at least one of the plurality of call objects the graphical user interface further enables recording by the healthcare provider custom media in the form of a message.

6. The information management and communications system of claim 5, wherein the plurality of call objects stored on the storage mechanism comprise at least one of each of the authentication messages, greeting messages, announcements, closing messages, conditional announcements, third-party announcements, notices, disclaimers, and conditional messages.

7. The information management and communications system of claim 1, wherein the graphical user interface further enables automatic contacting of the patient by the healthcare provider with the automated interactive patient response system.

8. The information management and communications system of claim 7, wherein the graphical user interface further enables scheduling by the healthcare provider when the patient is contacted with the automated interactive patient response system.

9. The information management and communications system of claim 1, wherein the computer network system further comprises:
   a predictive model for predicting an impending medical event of the patient, the computer network system performing the risk evaluation by evaluating the responses of the patient against the predictive model and thereby identifying any elevated risk levels of the patient, by ranking the elevated risk levels against other patients within the population of patients;
   wherein the computer network system stores the predicted impending medical event on the storage mechanism and enables accessing by the healthcare provider the predicted impending medical event stored on the storage mechanism.

10. The information management and communications system of claim 1, wherein the computer network system further comprises:
   predictive models for a plurality of diseases and conditions; and
   decision support tools used by the computer network system for performing the risk evaluation by evaluating at least one the responses of the patient against at least one of the predictive models for at least one of the plurality of diseases and conditions and thereby identifying any elevated risk levels of the patient, ranking the risk levels within the population of patients, and displaying the ranking of the risk levels to the healthcare provider.

11. A method for managing information and communications between a population of patients and healthcare providers and providing automated interactive health assessment monitoring of the population of patients using an information management and communications system that enables healthcare providers to selectively provide any of health screening, medical compliance, wellness program compliance, and disease management tailored for an individual patient within the population of patients, the method comprising:
   storing on a nontransitory storage mechanism of a computer network system a plurality of call objects comprising a plurality of health assessment questions and at least one message chosen from the group consisting of authentication messages, greeting messages, announcements, closing messages, conditional announcements, third-party announcements, interactive prompts, notices, disclaimers, and conditional messages;
   a healthcare provider using a graphical user interface of the computer network system and thereby interactively building an entire monitoring call dialog that is audible and tailored for an individual patient by
      selecting multiple call objects from the plurality of call objects including selecting the at least one message and selecting multiple health assessment questions from the plurality of health assessment questions,
      editing at least some of the multiple call objects including the multiple health assessment questions thereof and thereby further tailoring the entire monitoring call dialog for the individual patient,
      positioning and configuring the multiple call objects and the multiple health assessment questions thereof and thereby creating and configuring a sequence of elements of the monitoring call dialog and thereby further tailoring the monitoring call dialog for the individual patient, and
      saving the entire monitoring call dialog to the nontransitory storage mechanism;
   audibly communicating the entire monitoring call dialog to the individual patient with an automated interactive patient response system;
   the individual patient providing responses to the multiple health assessment questions with the automated interactive patient response system;
   recording the responses of the individual patient in the storage mechanism;
   performing a risk evaluation based on the responses of the individual patient by aggregating relative risk factors obtained by comparing the responses of the individual patient to comparative measures;
   storing the risk evaluation on the storage mechanism;
   accessing the responses of the individual patient and the risk evaluation stored on the storage mechanism; and then
   modifying the monitoring call dialog by editing at least one of the multiple health assessment questions and thereby further tailoring the entire monitoring call dialog to selectively provide any of health screening, medical compliance, wellness program compliance, and disease management of the individual patient.

12. A method for managing information and communications between a population of patients and healthcare providers and providing automated interactive health assessment monitoring of the population of patients and thereby selectively providing any of health screening, medical compliance, wellness program compliance, and disease management tailored for any individual patient within the population of patients, the method comprising:
   storing on a nontransitory storage mechanism of a computer network system a plurality of call objects comprising a plurality of health assessment questions and a plurality of messages chosen from the group consisting of authentication messages, greeting messages, announcements, closing messages, conditional announcements, third-party announcements, interactive prompts, notices, disclaimers, and conditional messages;
   a healthcare provider using a graphical user interface of the computer network system and thereby interactively building an entire monitoring call dialog that is audible and tailored for an individual patient by using the graphical user interface to
      select multiple call objects from the plurality of call objects including selecting multiple messages from the plurality of messages and multiple health assessment questions of the plurality of health assessment questions,
      edit at least some of the multiple call objects including the multiple health assessment questions thereof and thereby further tailoring the entire monitoring call dialog for the individual patient,
      position and configure the multiple call objects and the multiple health assessment questions thereof and thereby creating and configuring a sequence of elements of the monitoring call dialog and thereby further tailoring the monitoring call dialog for the individual patient, and save the entire monitoring call dialog to the storage mechanism;

audibly communicating the entire monitoring call dialog to the individual patient with an automated interactive patient response system;

the individual patient providing responses to the multiple health assessment questions with the automated interactive patient response system;

recording the responses of the individual patient in the storage mechanism;

performing a risk evaluation based on the responses of the individual patient by aggregating relative risk factors obtained by comparing the responses of the individual patient to comparative measures;

storing the risk evaluation on the storage mechanism;

accessing the responses of the individual patient and the risk evaluation stored on the storage mechanism; and then modifying the monitoring call dialog by editing at least one of the multiple health assessment questions and thereby further tailoring the monitoring call dialog to selectively provide any of health screening, medical compliance, wellness program compliance, and disease management of the individual patient.

13. The method of claim 12, wherein the computer network system is a provider-hosted computer network system comprising a server offsite from the graphical user interface, and the graphical user interface is connected to the storage mechanism and the server via the Internet.

14. The method of claim 12, the risk evaluation further comprising:

predicting an impending medical event of the patient by evaluating the responses of the patient against a predictive model and thereby identifying any elevated risk levels of the patient; and then ranking the elevated risk levels against other patients within the population of patients;

storing the predicted impending medical event on the storage mechanism; and the healthcare provider accessing the predicted impending medical event stored on the storage mechanism.

15. The method of claim 12, the risk evaluation further comprising:

using decision support tools and thereby evaluating the responses of the patient against predictive models for at least one of a plurality of diseases and conditions and thereby identifying any elevated risk levels of the patient;

ranking the risk levels within the population of patients; and displaying the ranking of the risk levels to the healthcare provider.

16. The method of claim 12, the method further comprising:

scheduling a frequency and duration for when the monitoring call dialog is audibly communicated to the patient with the automated interactive patient response system; and audibly communicating the monitoring call dialog to the patient with the automated interactive patient response system according to the scheduling step.

* * * * *